US00PP15094P3

(12) United States Plant Patent
Murakami

(10) Patent No.: US PP15,094 P2
(45) Date of Patent: Aug. 24, 2004

(54) PETUNIA PLANT NAMED 'SUNBELKOS'

(50) Latin Name: *Petunia hybrida*
Varietal Denomination: Sunbelkos

(75) Inventor: Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 66 days.

(21) Appl. No.: 10/326,967

(22) Filed: Dec. 24, 2002

(65) Prior Publication Data

US 2003/0131390 P1 Jul. 10, 2003

(30) Foreign Application Priority Data

Dec. 28, 2001 (JP) ..... 14310

(51) Int. Cl.[7] ..... A01H 5/00
(52) U.S. Cl. ..... Plt./356
(58) Field of Search ..... Plt./356

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP8,489 | P | 12/1993 | Hirabayashi et al. |
| PP8,768 | P | 6/1994 | Hirabayashi et al. |
| PP9,322 | P | 10/1995 | Tachibana et al. |
| PP9,341 | P | 10/1995 | Tachibana et al. |
| PP9,342 | P | 10/1995 | Sakazaki et al. |
| PP9,556 | P | 5/1996 | Tachibana et al. |
| PP9,557 | P | 5/1996 | Suzuki et al. |
| PP9,754 | P | 12/1996 | Suzuki et al. |
| PP10,045 | P | 9/1997 | Rother |
| PP10,278 | P | 3/1998 | Murakami |
| PP10,279 | P | 3/1998 | Murakami |
| PP10,287 | P | 3/1998 | Murakami |
| PP10,310 | P | 3/1998 | Sakazaki |
| PP10,330 | P | 4/1998 | Sakazaki |
| PP10,355 | P | 4/1998 | Murakami |
| PP10,904 | P | 5/1999 | Hansson |
| PP11,006 | P | 7/1999 | Danziger |
| PP11,352 | P | 4/2000 | Murakami |
| PP11,558 | P | 10/2000 | Murakami |
| PP12,101 | P2 | 9/2001 | Sakazaki |

*Primary Examiner*—Bruce R. Campell
*Assistant Examiner*—Michelle Kizilkaya
(74) *Attorney, Agent, or Firm*—Burns, Doane, Swecker & Mathis, L.L.P.

(57) ABSTRACT

Disclosed herein is a new and distinct variety of Petunia plant, having a semi-decumbent habit. The Petunia plant has abundant branching, particularly with respect to secondary branching, and great profusion of blooms with the entire plant remaining in bloom for a considerable period of time. The flowers are single and very small with the petals having a deep purplish pink~strong purplish pink ground color with a dark red center margin. The base color of the corolla throat is brilliant greenish yellow and the outside of the corolla tube is moderate olive. The plant exhibits high resistance to rain, heat, drought and diseases such as powdery mildew.

2 Drawing Sheets

Botanical/commercial classification: Petunia hybrida/Petunia Plant.
Varietal denomination: cv. 'Sunbelkos'.

BACKGROUND OF THE VARIETY

The Petunia is a very popular plant that is used for flower bedding and potting in the summer season. There are only a few small-flowered Petunias, such as, 'Suntory SP-R' (U.S. Plant Pat. No. 9,557), 'Sunberubu' (U.S. Plant Pat. No. 9,754), 'Sunbelchipi' (U.S. Plant Pat. No. 10,355), and 'Sunbeluki' (U.S. Plant Pat. No. 11,558). These Petunias are of the semi-decumbent type and have a medium plant height, abundant branching, and a high resistance to heat, rain and disease. However, there are only a few varieties having a great profusion of flowers, a deep purplish-pink flower color, a very small flower size, and a high resistance to rain, heat, and disease. Accordingly, this invention is aimed at obtaining a new variety having a deep purplish-pink colored petals with a dark red center, and very small flowers combined with the above features.

The new variety of Petunia plant according to this invention originated from crossing with the Petunia variety named 'Sunbelchipi' (U.S. Plant Pat. No. 10,355) as the female parent and a Petunia plant variety named 'P54' (non-patented in the United States) as the male parent.

Initially, the crossing was conducted in May 1997 at the Omi R&D Center of SUNTORY Ltd., located at 863-1, Aza-Iketani, Omori-cho, Youkaichi-shi, Shiga-ken, Japan. From that crossing, 50 seedlings were obtained and five seedlings were selected during September 1998 in view of their semi-erect growth habit and deep purplish-pink colored petals. These five seedlings were grown and were tested during potting and bedding trials. Only one plant was selected in September 1999. The selected plant was propagated by the use of cuttings and then grown in pots in a trial in a greenhouse and in the field at the Omi R&D Center from April to November 2000. The botanical characteristics of the finally selected plant were examined using a similar variety, 'Sunbelbipi' variety (non-patented in the United States), for comparison. As a result, it was concluded that this new Petunia variety is distinguishable from any other variety whose existence is known to us and is uniform and stable in its characteristics. This new variety of Petunia plant was named 'Sunbelkos'.

The new variety of the present invention can be readily distinguished from the 'Sunbelrikupi' variety (U.S. Plant patent application Ser. No. 10/327,017, filed Dec. 24, 2002)

and the 'Sunbelre' variety (U.S. Plant patent application Ser. No. 10/327,030, filed Dec. 24, 2002) through an observation of the flower coloration. Each of these varieties had the same female parent. The new 'Sunbelkos' variety of the present invention forms deep purplish-pink flowers with a dark red center, the 'Sunbelrikupi' variety forms vivid reddish-purple flowers, and 'Sunbelre' variety forms deep red flowers.

In the following description, the color information is in accordance with The R.H.S. Colour Chart of The Royal Horticultural Society, London, England. A color chart based on The Japan Color Standard for Horticultural Plants (J.H.S. Color Chart) is also added for reference.

The main botanical characteristics 'Sunbelchipi' female parent are as follows:

Plant:
- *Growth habit.*—Semi-decumbent.
- *Plant height.*—Approximately 15–16 cm.
- *Spreading area of plant.*—The stem extends to a length of approximately 11–13 cm from the base.
- *Blooming period.*—April to late October in the southern Kanto area, Japan. The plant shape does not change throughout this period.

Stem:
- *Thickness.*—Approximately 2.3 mm.
- *Pubescence.*—Present.
- *Branching.*—Abundant with the superior branching propensity, especially secondary branches.
- *Length of internode.*—Approximately 1.4 cm.

Leaf:
- *Shape.*—Lanceolate.
- *Length.*—Approximately 5.1 cm.
- *Width.*—Approximately 1.6 cm.
- *Color.*—Dark yellow green (R.H.S. 146A, J.H.S. 3508).
- *Thickness.*—Approximately 0.2–0.4 mm.
- *Pubescence.*—Sparse.
- *Leaf attachment angle to stem.*—Slanted upward to horizontal.

Flower:
- *Facing direction.*—Horizontal.
- *Type.*—Single.
- *Shape.*—Funnel-shaped, with five fissures.
- *Shape of petal tip.*—Round.
- *Waving of petal.*—Weak.
- *Lobation of petal.*—Shallow.
- *Diameter.*—Approximately 2.8–2.9 cm.
- *Color.*—Petal: Vivid purplish-red (R.H.S. 57C, J.H.S. 9707). Bottom color of corolla throat: Strong yellow (R.H.S. 9A, J.H.S. 2513). Outside color of corolla tube: Light greenish-yellow (R.H.S. 5C, J.H.S. 2904).
- *Reproductive organs.*—1 normal pistil and 5 normal stamens.
- *Fertility.*—Fertile, but self-incompatible.
- *Peduncle.*—Approximately 0.7–0.8 mm in thickness, and approximately 1.9 cm in length.
- *Physiological and ecological characteristics.*—High resistance to heat, rain, drought and diseases, such as powdery mildew. The resistance to heat and rain is very strong.
- *Blooming.*—A bloom commonly lasts approximately 10 days on the plant. Pinching is not necessary to ensure continuous blooming; however, it does tend to enhance bloom production.

The main botanical characteristics of the 'P54' variety are as follows:

Plant:
- *Growth habit.*—Decumbent.
- *Plant height.*—Approximately 9 cm.
- *Spreading area of plant.*—The stem extends to a length of approximately 8 cm from the base.
- *Blooming period.*—April to late October in the southern Kanto area, Japan. The plant shape does not change throughout this period.

Stem:
- *Thickness.*—Approximately 2.1 mm.
- *Pubescence.*—Sparse.
- *Branching.*—Abundant with a superior branching propensity, especially secondary branches.
- *Length of internode.*—Approximately 0.4 cm.

Leaf:
- *Shape.*—Lanceolate.
- *Length.*—Approximately 3.2 cm.
- *Width.*—Approximately 1.0 cm.
- *Color.*—Deep yellow-green (R.H.S. 137C, J.H.S. 3706).
- *Thickness.*—Approximately 0.3 mm.
- *Pubescence.*—Sparse.
- *Leaf attachment angle to stem.*—Slanted upward to horizontal.

Flower:
- *Facing direction.*—Upward to slanted upward.
- *Type.*—Single.
- *Shape.*—Funnel-shaped, with five fissures.
- *Shape of petal tip.*—Round.
- *Waving of petal.*—Weak.
- *Lobation of petal.*—Shallow.
- *Diameter.*—Approximately 3.0 cm.
- *Color.*—Petal: Pale purplish-pink (R.H.S. 69C, J.H.S. 9501) ground color with strong reddish-purple (R.H.S. 70A, J.H.S. 9214) veins, light reddish-purple (R.H.S. 78C, J.H.S. 9212) center and with deep purplish-pink (R.H.S. 73A, J.H.S. 9205) streaks. Bottom color of corolla throat: Brilliant greenish-yellow (R.H.S. 5A, J.H.S. 2905). Outside color of corolla tube: Light greenish-yellow (R.H.S. 5C, J.H.S. 2904).
- *Reproductive organs.*—1 normal pistil and 5 normal stamens.
- *Fertility.*—Fertile, but self-incompatible.
- *Peduncle.*—Approximately 0.8 mm in thickness, and approximately 2.0 cm in length.
- *Physiological and ecological characteristics.*—High resistance to heat, rain, drought and diseases, such as powdery mildew. The resistance to heat and rain is very strong.
- *Blooming.*—A bloom commonly lasts approximately 10 days on the plant. Pinching is not necessary to ensure continuous blooming; however, it does tend to enhance bloom production.

The main botanical characteristics 'Sunbelbipi' variety are as follows:

Plant:
- *Growth habit.*—Semi-erect.
- *Plant height.*—Approximately 16 cm.
- *Spreading area of plant.*—The stem extends to a length of approximately 9 cm from the base.

*Blooming period.*—April to late October in the southern Kanto area, Japan. The plant shape does not change throughout this period.

Stem:

*Thickness.*—Approximately 2.2 mm.

*Pubescence.*—Present.

*Branching.*—Abundant with a superior branching propensity, especially secondary branches.

*Length of internode.*—Approximately 1.4 cm.

Leaf:

*Shape.*—Lanceolate to elliptic.

*Length.*—Approximately 3.9 cm.

*Width.*—Approximately 2.0 cm.

*Color.*—Grayish olive-green (R.H.S. 137B, J.H.S. 3716).

*Thickness.*—Approximately 0.2–0.4 cm.

*Pubescence.*—Sparse.

*Leaf attachment angle to stem.*—Slanted upward to horizontal.

Flower:

*Facing direction.*—Horizontal.

*Type.*—Single.

*Shape.*—Funnel-shape, with five fissures.

*Shape of petal tip.*—Round.

*Waving of petal.*—Weak.

*Lobation of petal.*—Shallow.

*Diameter.*—Approximately 3.5 cm.

*Color.*—Petal: Vivid reddish-purple (R.H.S. 65D, J.H.S. 9207). Bottom color of corolla throat: Brilliant greenish-yellow (R.H.S. 5A, J.H.S. 2905).

*Outside color of corolla tube.*—Light yellow-green (R.H.S. 154C, J.H.S. 3103).

*Reproductive organs.*—1 normal pistil and 5 normal stamens.

*Fertility.*—Fertile, but self-incompatible.

*Peduncle.*—Approximately 0.8 mm in thickness, and approximately 2.2 cm in length.

*Physiological and ecological characteristics.*—High resistance to heat, rain, drought and diseases, such as powdery mildew. The resistance to heat and rain is very strong.

*Blooming.*—A bloom commonly lasts approximately 10 days on the plant. Pinching is not necessary to ensure continuous blooming; however, it does tend to enhance bloom production.

SUMMARY OF THE VARIETY

This new variety of Petunia plant 'Sunbelkos' has a semi-decumbent growth habit with abundant branching, and forms single, very small deep purplish-pink flowers with a dark red center in a great profustion of blooms with the entire plant remaining in bloom for a considerable period of time. The plant has high tolerances to cold and heat, high resistance to pests and diseases, particularly powdery mildew, and high resistance to rain.

The plants described and depicted herein were propagated by the use of cuttings and were approximately nine months of age. Such cuttings were placed in a greenhouse in January, were transplanted in February, were further transplanted to pots in April and were thereafter placed outdoors, and were trimmed during July. When present in a greenhouse, the plants were grown under controlled greenhouse conditions under full sunshine with no shielding from light. The minimum greenhouse temperature was maintained above 13° C.

BRIEF DESCRIPTION OF THE PHOTOGRAPHS

The depicted plants had been reproduced by the use of cuttings and were photographed during September while growing outdoors in pots at an age of approximately nine months at Youkaichi-shi, Shiga-ken, Japan.

DESCRIPTION OF THE NEW VARIETY

The botanical characteristics of the new and distinct variety of Petunia plant named 'Sunbelkos' are as follows were observed during October at Youkaichi-shi, Shiga-ken, Japan:

Plant:

*Growth habit.*—Semi-decumbent.

*Plant height.*—Approximately 14 cm.

*Spreading area of plant.*—The stem extends to a length of approximately 8 cm from the base.

*Blooming period.*—April to late October in the southern Kanto area, Japan. The plant shape does not change throughout this period.

Stem:

*Thickness.*—Approximately 2.4 mm.

*Pubescence.*—Sparse.

*Branching.*—Abundant with a superior branching propensity, especially with respect to secondary branches.

*Length of internode.*—Approximately 1.1 cm.

Leaf:

*Shape.*—Lanceolate.

*Length.*—Approximately 4.1 cm.

*Width.*—Approximately 1.2 cm.

*Color.*—Dark olive-green (R.H.S. 137B, J.H.S. 3707) on the upper surface and R.H.S. 146B on the under surface.

*Venation.*—Pinnate and R.H.S. 150A.

*Texture.*—Smooth.

*Margin.*—Entire.

*Thickness.*—Approximately 0.4 mm.

*Pubescence.*—Sparse.

*Leaf attachment angle to stem.*—Slanted upward to horizontal.

Flower:

*Facing direction.*—Slanted upward.

*Type.*—Single.

*Shape.*—Funnel-shape, with five fissures.

*Shape of petal tip.*—Round.

*Waving of petal.*—Weak.

*Lobation of petal.*—Shallow.

*Diameter.*—3.0 cm.

*Color.*—Petal: Deep purplish-pink (R.H.S. 57D, J.H.S. 9705 to R.H.S. 58D, J.H.S. 9704) with a dark red (R.H.S. 59D, J.H.S. 0110) center. The base color of corolla throat: Brilliant greenish-yellow (R.H.S. 8A, J.H.S. 2704). Outside color of corolla tube: Light greenish-yellow (R.H.S. 5C, J.H.S. 2904).

Figure 1:
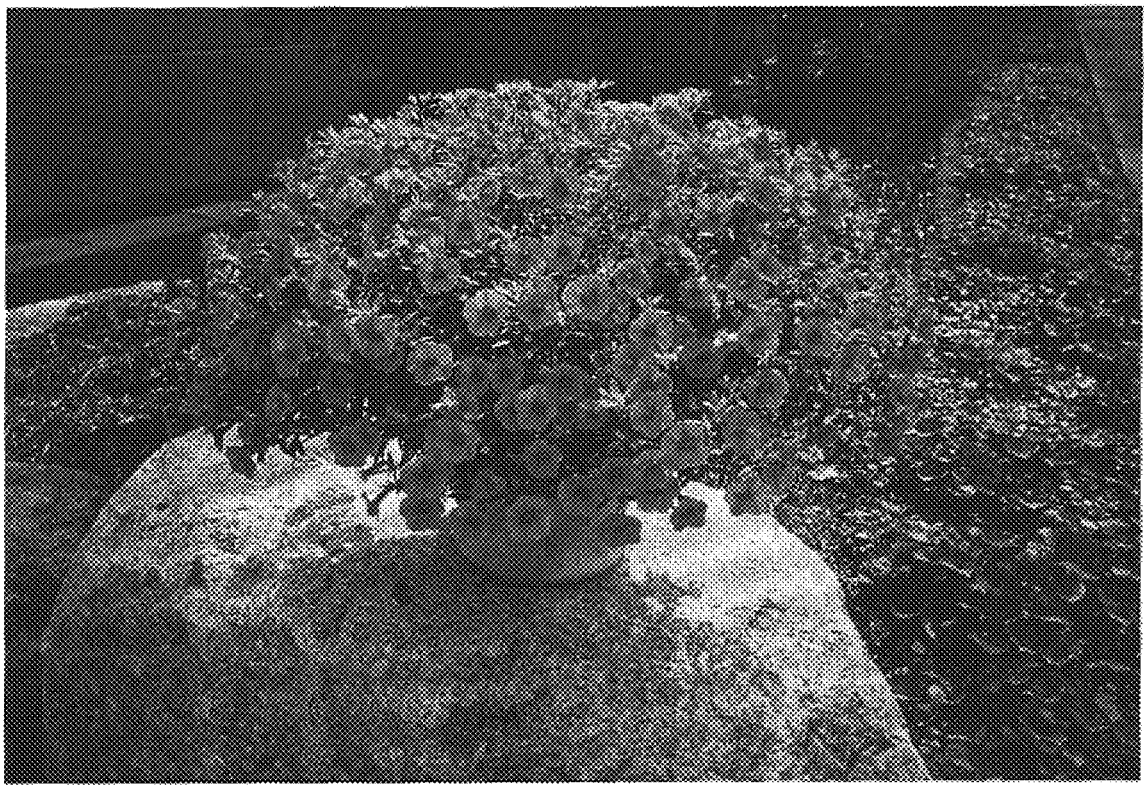
FIG. 1 is a photograph of flowers and leaves of the new variety of Petunia plant 'Sunbelkos'.
Figure 2:
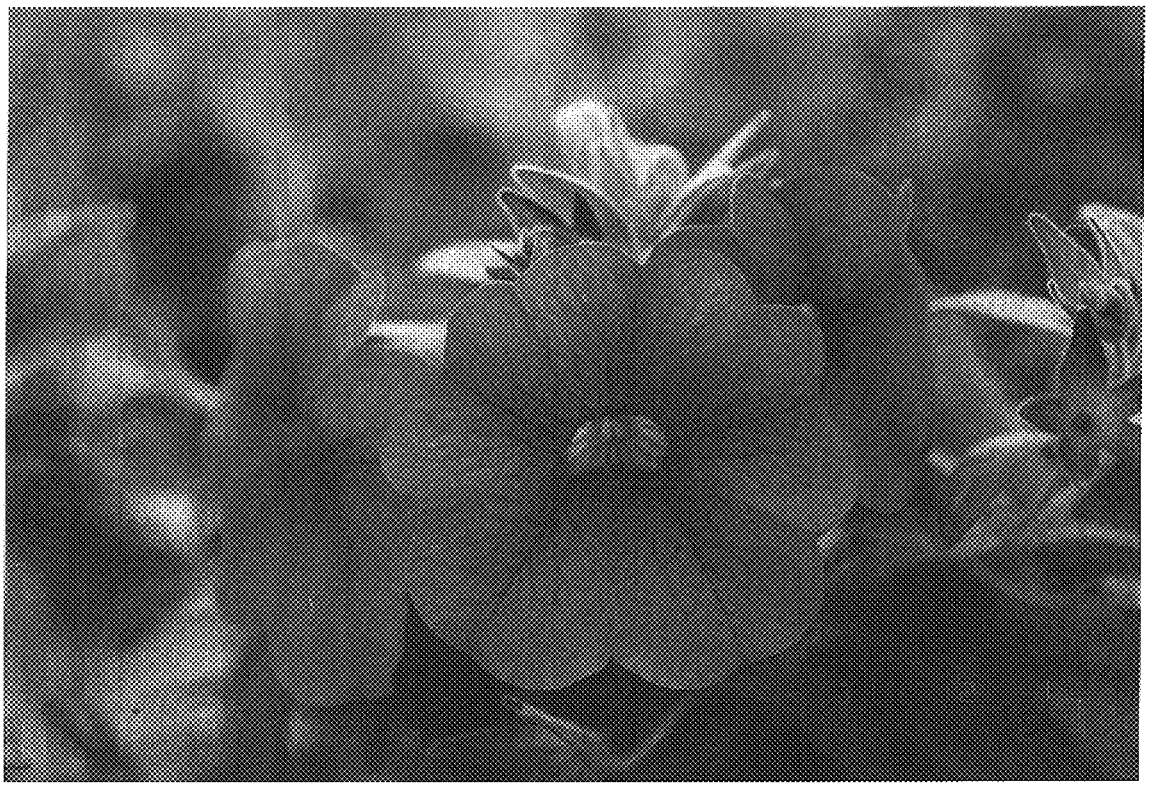
FIG. 2 is a photograph of flowers of the new variety of Petunia plant 'Sunbelkos'.

*Venation.*—R.H.S. 59B in coloration, and with generally linear main veins with much branching as illustrated in FIG. 2.

*Sepals.*—R.H.S. 144A on the upper and lower surface in coloration, generally lanceolate in configuration, with an entire margin, approximately 11.5 mm in length, approximately 2.7 mm in width at the widest point, and five in number. The calyx is tubular and divides into five sepals.

*Seeds.*—R.H.S. 186A in coloration, approximately 0.6 mm in diameter, and generally round. The quantity is typical of Petunia hybrida.

*Reproductive organs.*—1 normal pistil and 5 normal stamens. The stigma is club-shaped and R.H.S. 145A in coloration. The style is approximately 8 mm in length and R.H.S. 145D in coloration. The ovary is R.H.S. 145B in coloration. The stamens commonly are of variable lengths from approximately 6.8 to 12 mm. Pollen is formed in a quantity that is typical of Petunia hybrida and is near R.H.S. 17A in coloration.

*Fertility.*—Fertile, but self-incompatible.

*Peduncle.*—Approximately 0.8 mm in thickness, and approximately 1.8 cm in length. R.H.S. 177A on the upper side, and R.H.S. 144B on the lower side. The texture is smooth.

*Physiological and ecological characteristics.*—High resistance to heat, rain, drought and diseases, such as Powdery mildew. The resistance to heat and rain is very strong.

*Blooming.*—A bloom commonly lasts approximately 10 days on the plant. Pinching is not necessary to ensure continuous blooming; however, it does tend to enhance bloom production.

This new variety of Petunia plant is most suitable for flower bedding and potting, particularly in hanging pots or in planters, and is excellent for use as a ground cover. Pinching of old blossoms will enhance the formation of new blossoms.

I claim:

1. A new and distinct variety of Petunia plant, substantially as herein illustrated and described, characterized particularly as to novelty by (A) having a semi-decumbent growth habit, (B) great profusion of blooms with the entire plant remaining in bloom for a considerable period of time, (C) flowers are single and very small, petals have a deep purplish pink~strong purplish pink ground color with a dark red center margin, and (D) a high resistance to rain, heat, drought and disease such as powdery mildew.

* * * * *